(12) United States Patent
Foley

(10) Patent No.: US 8,029,830 B2
(45) Date of Patent: Oct. 4, 2011

(54) COMPOSITION AND METHOD FOR PROMOTING INTERNAL HEALTH AND EXTERNAL APPEARANCE

(75) Inventor: Ryan Jason Foley, Toronto (CA)

(73) Assignee: Nuvocare Health Services Inc., Toronto, Ontario (CA)

( * ) Notice: Subject to any disclaimer, the term of this patent is extended or adjusted under 35 U.S.C. 154(b) by 0 days.

(21) Appl. No.: 12/350,305

(22) Filed: Jan. 8, 2009

(65) Prior Publication Data

US 2009/0263367 A1    Oct. 22, 2009

Related U.S. Application Data

(60) Provisional application No. 61/046,067, filed on Apr. 18, 2008.

(51) Int. Cl.

| | |
|---|---|
| *A61K 36/00* | (2006.01) |
| *A61K 31/575* | (2006.01) |
| *A61K 36/704* | (2006.01) |
| *A61K 31/375* | (2006.01) |
| *A61K 31/355* | (2006.01) |
| *A61K 31/455* | (2006.01) |
| *A61K 36/48* | (2006.01) |
| *A61K 38/44* | (2006.01) |
| *A61K 36/82* | (2006.01) |
| *A61K 33/04* | (2006.01) |
| *A61K 31/34* | (2006.01) |
| *A61K 38/28* | (2006.01) |

(52) U.S. Cl. ....... 424/725; 424/94.4; 424/729; 424/757; 424/702; 514/474; 514/458; 514/6.4

(58) Field of Classification Search .................. None
See application file for complete search history.

(56) References Cited

U.S. PATENT DOCUMENTS

| | | | |
|---|---|---|---|
| 2004/0001817 A1* | 1/2004 | Giampapa | 424/94.1 |
| 2004/0161524 A1 | 8/2004 | Sakai et al. | |
| 2004/0208902 A1* | 10/2004 | Gupta | 424/401 |
| 2006/0165636 A1 | 7/2006 | Hasebe et al. | |

FOREIGN PATENT DOCUMENTS

| | | | |
|---|---|---|---|
| CN | 1712036 A | * | 12/2005 |
| CN | 101053409 A | * | 10/2007 |
| GB | 2381451 A | * | 5/2003 |
| JP | 08176005 A | * | 7/1996 |

OTHER PUBLICATIONS

Vouldoukis et al, Antioxidant and anti-inflammatory properties of a *Cucumis melo* LC. extract rich in superoxide dismutase activity, Journal of ethnopharmacology, (Sep. 2004) vol. 94, No. 1, pp. 67-75.*

Letchamo et al, Variations in chemical content and antioxidative properties of wild and cultivated *Rhodiola rosea* L. roots, Abstracts of Papers, 226th ACS National Meeting, New York, NY, United States, Sep. 7-11, 2003.*

Li et al, Chemical constituents and pharmacological research of *Fordia cauliflora*, Zhongyao Xinyao Yu Linchuang Yaoli (2005), 16(3), 231-232, C3.*

* cited by examiner

*Primary Examiner* — Qiuwen Mi

(74) *Attorney, Agent, or Firm* — Lorelei Graham

(57) ABSTRACT

The present invention relates to a new composition comprising substances that promote DNA repair, reduce body fat levels and increase lean body mass and that decrease wrinkle appearance and/or improvement in skin surface. In some aspects, the composition of the present invention include resveratrol, forskohlin and astaxanthin. In another aspect the composition of the present invention further comprises carboxy alkyl ester. The present invention also relates to a method of promoting internal health and external appearance in a subject in need, said method comprising administering to the subject a composition that promotes DNA repair, reduces body fat levels and increases lean body mass and that decreases wrinkle appearance and/or improvement in skin surface.

28 Claims, No Drawings

COMPOSITION AND METHOD FOR PROMOTING INTERNAL HEALTH AND EXTERNAL APPEARANCE

This application claims priority of Provisional Application Ser. No. 61/046,067, filed Apr. 18, 2008, entitled Composition and Method for Promoting Internal Heath and External Appearance, the entire disclosure of which is incorporated herein by reference

FIELD OF THE INVENTION

The present invention relates generally to a composition, a method of using said composition, and a process of manufacturing the composition offering health benefits, and, more particularly, to a blend of botanical extracts, vitamins, amino acids, minerals and neuroprotectants for promoting internal health and promoting external appearance.

BACKGROUND OF THE INVENTION

As we age, our bodies undergo a variety of changes. These changes can frequently interact with each other to produce compounding effects. Three major causes of human-ageing include gene expression deficiency at the cellular level, muscle degeneration at the muscular level, and free-radical production at the skin surface level.

While some of these age-related changes are inevitable, they can also result from nutritional deficiencies and lifestyle patterns. For example, the human skin is constantly exposed to numerous physical, chemical and environmental stressors, some of which directly or indirectly adversely affect the skin. Cutaneous overexposure to environmental solar ultraviolet (UV) radiation has a variety of adverse effects on human health, including the development of melanoma and non-melanoma skin cancers. Environmental pollutants and UV light are also key factors that contribute to the structural damage of the skin's vital components, and the resultant appearance of fine lines and wrinkles.

A number of therapies exist for promoting DNA repair, for improving lean body composition (decreasing body fat and maintaining lean body tissue), for promoting skin health and help reduce the appearance of wrinkles, including surgical intervention, intervention with diet, exercise and dietary supplement programs are frequently instituted.

However, no single therapy in use today has demonstrated an ability to reliably enhance DNA repair, decrease body fat, increase lean body mass, promote skin health and help reduce the appearance of wrinkles. Therefore, there exists a currently unmet need in the art for an effective composition and method to promote overall internal health via cellular DNA repair, improvement in lean body mass and reduce body fat levels, and external appearance improvements via promoting skin health or helping reduce the appearance of wrinkles. Thus, a treatment means that can be orally administered and that can effectively stabilize and/or enhance the adverse effects of ageing and exposure to environmental factors that contribute to the structural damage of the skin of patients would be of considerable benefit. The present invention discloses such a composition and method.

SUMMARY OF THE INVENTION

The present inventors have now discovered that a combination of components as described herein, provides an effective treatment to promote overall internal health and external appearance. Internal health and external appearance are promoted by promoting DNA repair, reducing body fat levels, increasing lean body mass and helping promote skin health or helping reduce the appearance of wrinkles.

In one aspect, the present invention is a composition comprising resveratrol, forskohlin and astaxanthin.

In another aspect, the present invention is a composition comprising resveratrol, forskohlin, astaxanthin and an antioxidant selected from the group consisting of carboxy alkyl ester and superoxide dismutase.

In yet another aspect, the present invention is a composition comprising resveratrol, forskohlin, astaxanthin and superoxide dismutase.

In yet a further aspect, the present invention is a composition comprising resveratrol, forskohlin, astaxanthin and carboxy alkyl ester.

In yet another aspect, the present invention is a composition comprising resveratrol, forskohlin, astaxanthin, carboxy alkyl ester, beta-alanine, a neuroprotectant, epigallocatechin-gallate (EGCG), rosavins and salidrosides.

In yet another aspect of the present invention is a composition comprising an *Uncaria tomentosa* extract containing carboxy alkyl esters; a *glycine max* extract containing beta-sitosterol; a *Polygonum cuspidatum* extract containing resveratrol; an *Indian colchicum* extract containing forskohlin; a green tea extract containing EGCG; an *Haematococcus pluvialis* extract containing astaxanthin; and a *Rhodiola rosea* extract containing rosavins and salidrosides, a neuroprotectant and a beta-alanine.

In yet a further aspect, the composition of the present invention further comprises a vitamin and/or mineral preparation. In one aspect, the vitamin and/or mineral preparation includes: vitamin C, vitamin D, vitamin E, niacin, vitamin B6, folic acid, vitamin B12, an effective selenium and zinc.

In yet another aspect, the composition of the present invention is presented in an oral daily unit dosage form.

In yet another aspect, the composition of the present invention comprises an oral daily unit dosage form of: about 100 mg to about 400 mg of the *Uncaria tomentosa* extract standardized to about 8% of carboxy alkyl ester, about 100 mg to about 400 mg of *glycine max* extract standardized to about 40% beta-sitosterol, about 25 mg to about 200 mg of the *Polygunum cuspidatum* extract standardized to about 50% resveratrol, about 50 mg to about 500 mg of beta-alanine, about 25 mg to about 200 mg of the *Indian colchicum* extract standardized to about 40% forskohlin, about 0 mg to about 150 mg of caffeine, about 200 mg to about 1000 mg of the green tea extract standardized to about 98% polyphenols, 80% catechins and 45% EGCG, about 100 mg to 1000 mg of the *Haematococcus pluvialis* extract standardized to about 2% astaxanthin, and about 50 mg to about 500 mg of the *Rhodiola rosea* extract standardized to about 3% rosavins and 1% salidrosides.

In yet another aspect, the composition of the present invention comprises an oral daily unit dosage of about 100 mg to about 900 mg of cantaloupe melon extract standardized for superoxide dismutase.

In one aspect, the present invention is a method for promoting internal health and external appearance in a subject in need, said method comprising administering to the subject a composition comprising substances that promote DNA repair, reduce body fat levels and increase lean body mass and that promotes skin health or helps reduce the appearance of wrinkles.

In another aspect, the present invention is a method for promoting internal health and external appearance in a subject in need, said method comprising administering to the subject a composition comprising resveratrol, forskohlin and astaxanthin. In one aspect, the composition of the method of the invention further comprises an antioxidant selected from the group consisting of carboxy alkyl ester and a superoxide dismutase.

In yet another aspect, the present invention is a method for promoting internal health and external appearance in a subject in need, said method comprising administering to the subject a composition comprising resveratrol, forskohlin, astaxanthin and superoxide dismutase.

In yet another aspect, the present invention is a method for promoting internal health and external appearance in a subject in need, said method comprising administering to the subject a composition comprising resveratrol, forskohlin, astaxanthin and carboxy alkyl ester.

In yet a further aspect of the present invention is a method for promoting internal health and external appearance in a subject in need, said method comprising administering to the subject a composition comprising resveratrol, forskohlin, astaxanthin, carboxy alkyl ester, beta-alanine, a neuroprotectant, epigallocatechin-gallate (EGCG), rosavins and salidrosides.

In yet another aspect, the method of the present invention comprises administering the subject in need a composition comprising an extract having carboxy alkyl ester, an extract having beta-sitosterol, an extract having resveratrol, beta-alanine, an extract having forskohlin, a neuroprotectant, an extract having epigallocatechin-gallate (EGCG), an extract having astaxanthin, and an extract having rosavins and salidrosides.

In yet another aspect the composition of the method of the invention further comprises a vitamin and/or mineral preparation. In one aspect the vitamin and/or mineral preparation comprises: vitamin C, vitamin D, vitamin E, niacin, vitamin B6, folic acid, vitamin B12, selenium and zinc.

Advantages of the present invention include the reactivation of youth, increase skin rejuvenation and increase skin firmness with the following key benefits: enhanced DNA repair, improve lean body composition and promote skin health or reduce the appearance of wrinkles.

DETAILED DESCRIPTION OF THE INVENTION

Reference is now made to a specific aspect of the present invention, which illustrates the best mode presently contemplated by the inventors for practicing the invention. Alternative aspects are also briefly described as applicable.

The present invention relates to compositions, methods of using the compositions and methods of manufacturing the compositions.

The present invention relates to a composition comprising resveratrol, forskohlin and astaxanthin. In one aspect, the composition of the present invention further comprises carboxy alkyl ester and superoxide dismutase.

In one aspect, the composition of the present invention comprises: carboxy alkyl ester, resveratrol, forskohlin, and astaxanthin.

In yet another aspect, the present invention relates to a composition comprising: carboxy alkyl ester, beta-sitosterol, resveratrol, beta-alanine, forskohlin, a neuroprotectan, epigallocatechin-gallate (EGCG), astaxanthin, rosavins and salidrosides.

The composition may take the form of a swallowable nutricosmetic pill.

In one aspect of the present invention, the composition comprises a unique combination of seven botanical extracts, a neuroprotectant and an amino acid. This unique combination is referred to as NU-100™. With reference to Table 1, one aspect of the present invention, the composition comprises an extract having beta-sitosterol, an extract having resveratrol, an extract having forskohlin, an extract having epigallocatechin-gallate (EGCG), an extract having astaxanthin, an extract having rosavins and salidorsides, beta-alanine, caffeine and extract having carboxy alkyl ester.

TABLE 1

NU-100 ™ % by weight basis Breakdown

| Ingredients | % by weight breakdown |
|---|---|
| Green Tea Extract (*Camellia sinensis*) (leaf) [Standardized to 98% Polyphenols, 80% Catechins, 45% EGCG] | 34-35 |
| Cat's Claw Extract (*Uncaria tomentosa*)(bark) [Standardized to 8% Carboxy Alkyl Esters] | 14-15 |
| Soybean Phytosterol Extract (*Glycine max*) [Standarized to 40% Beta-sitosterol 20% Campesterol 14% Stigmasterol] | 8-9 |
| Deep Red Microalgae Extract (*Haematococcus pluvialis*) [Standardized to 2% Astaxanthin] | 11-12 |
| Coleus Forskholii Extract (Indian colchicum) (root) [Standardized to 40% Forskolin] | 7-8 |
| *Rhodiola* Extract (root) [Standarized to 3% Rosavin and 1% Salidrosides] | 5-6 |
| Japanese Knotwood (*Polygonum cuspidatum*) (root)[Standardized to 50% (25 mg) Trans-Resveratrol] | 5-6 |
| Beta-Alanine [99% β-Alanine] | 5-6 |
| Caffeine USP [15% overage] | 5-6 |

The compounds of NU-100™ are proven to control the three major causes of human-ageing by working directly at the core levels of the body:

LEVEL #1—Genetic DNA Level. The group of compounds at level #1 include: an extract having carboxy-alkyl-esters, an extract having resveratrol and an extract having beta-sitosterol. In one aspect the extract having carboxy alkyl ester is an *Uncaria tomentosa* extract, the extract having beta-sitosterol is a *glycine max* extract and the extract having resveratrol is a *Polygonum cuspidatum* extract. The group of ingredients of level #1 is referred to as NUVOCELL™. Each component of NUVOCELL™ works synergistically to promote internal health via an enhancement in DNA repair. For example, research completed at the University of Lund, Sweden, shows that oral delivery of *Uncaria tomentosa* extract having carboxy alkyl esters enhances DNA repair by 12%, promotes mitogenic response and leukocyte recovery after chemotherapy induced DNA damage in vivo (Sheng, Y. et al, 2001). Clinical research support for the other components of NUVOCELL™, are provided bellow herein.

LEVEL #2—Muscle Tissue level. The group of ingredients at level #2 include: an extract having forskholin (colforsin), a neuroprotectant and beta-alanine. In one aspect the extract having forskholin is an *Indian colchicum* extract. In another aspect of the present invention the neuroprotectant is selected from the group consisting of caffeine and Cha de Bugre. The group of ingredients of level #2 is referred to as NUVOFIT™. Each ingredient of NUVOFIT™ works synergistically to improve lean body mass composition. NUVOFIT™ works to effectively alleviate Lose Skin Syndrome (LSS) resulting from excess body-fat and poor muscletone. Forskholin is clinically proven to improve lean body composition by reducing body fat stores and increasing lean body weight. For example, oral ingestion of forskholin for 12 weeks was shown to significantly decrease body fat percentage while increasing lean body mass (Godard, M. et al, 2005).

Clinical research support for the other components of NUVOFIT™ are provided bellow herein.

LEVEL #3—Skin Surface Level. The group of ingredients at level #3 include: an extract having astaxanthin, an extract having epigallocatechin-gallate (EGCG) and an extract having rosavins and salidrosides. In one aspect the extract having astaxanthin is a Deep red mircroalgae (*Haematococcus pluvialis*) extract, the extract having EGCG is a green tea extract and the extract having the rosavins and salidrosides is a *Rhodiola* extract. The group of ingredients of level #3 is referred to as NUVODERM™. Each component of NUVODERM™ acts synergistically to improve skin surface health from the inside-out. For example, oral delivery of astaxanthin to test subjects has been shown to result in a 54% reduction in wrinkles and a 52% improvement in skin-surface-moisture after only 6 weeks (Yamashita, E., Carotenoid Science, vol. 10, (2006) pp 91-95). Other clinical research support for the other components of NUVODERM™ are provided bellow herein.

In one aspect of the present invention, the composition of the present invention is combined with vitamins and minerals. The combined composition of NU-100™ with the vitamins and minerals is referred to as AGEOFF™. In one aspect, the vitamins and minerals comprise vitamin C, vitamin D, vitamin E, niacin, vitamin B6, folic acid, vitamin B12, zinc and selenium.

TABLE 2

VITAMIN/MINERAL % by weight-basis breakdown

| Ingredients | % by Weight Breakdown |
|---|---|
| [1]Vitamin C (as calcium ascorbate) [82% Vitamin C] [50% RDI] | 25-26 |
| [1]Vitamin D3 powder (Cholecalciferol) [100% Vitamin D] [100% RDI] | 2-3 |
| [1]Vitamin E (51% tocopheryl acetate) [50% RDI] | 13-14 |
| [1]Folic acid (97%) [100% RDI] | 2-3 |
| [1]Vitamin B3 (Niacin) [99%][50% RDI] | 7.13 grams |
| 1Vitamin B6 (Pyridoxine hydrochloride) [81%][50% RDI] | 0.87 grams |
| [1]Vitamin B12 (Cyanocobalamin) [99%] [50% RDI] | 0.001-0.003 |
| [2]Selenium (L-selenomethionine) [2%] [50% RDI] | 1-2 |
| [2]Zinc Chelate (20% zinc) [100% RDI] | 48-49 |

[1]Includes 15% overage.
[2]Included 5% overage

In another aspect of the present invention, the composition of the present invention further comprises at least one of the following: a pharmaceutically acceptable carrier; a coloring agent, for example chlorophyllin copper complex; an emulsifier, an excipient, a flavouring agent; or any combinations thereof.

The term "pharmaceutically acceptable" as used herein means to be compatible with the treatment of animals, in particular humans.

Table 3, which show the components and formulation of one aspect of the present invention. In one aspect, the recommended dose of the composition of the invention is 2 capsules taken twice daily, for a total daily intake of 4 capsules. This dosing regimen is supported by current literature, as outlined in Table 3.

TABLE 3

| Medicinal Ingredients | Minimum dose per day | Maximum dose per day | References |
|---|---|---|---|
| Vitamin C | 6 mg | 2000 mg | Vitamin C: 6-2000 mg/day (NHPD monograph: vitamin C) Vitamin C: 2 g/day, in combination with vitamin E (1200 IU/day) (Mireles-Rocha et al. 2002) Vitamin C: 2 g/day, in combination with vitamin E (1000 IU/day) (Eberlein-Konig et al. 1998) |
| Vitamin D | 32 IU | 1000 IU | Vitamin D: 32-1000 IU/day (NHPD monograph: vitamin D) |
| Vitamin E | 10 IU | 400 IU | Vitamin E: 100 mg/day (Cadenas et al. 1996) Vitamin E (alpha-tocopheryl acetate): 400 IU/day, in combination with vitamin C (1 g/day) (Mastaloudis et al. 2004) |
| Niacin | 6 mg | 35 mg | Niacin: 6-35 mg/day (NHPD monograph: niacin) |
| Vitamin B6 | 0.1 mg | 100 mg | Vitamin B6: 0.1-100 mg/day (NHPD monograph: Vitamin B6). |
| Folic Acid | 10 mcg | 1000 mcg | Folic Acid: 30-1000 mcg/day (NHPD monograph: folic acid). |
| Vitamin B12 | 2 mcg | 1000 mcg | Vitamin B12: 2-1000 mcg/day (NHPD monograph: vitamin B12) |
| Zinc | 1 mg | 40 mg | Zinc: up to 40 mg/day (NHPD monograph: zinc) Zinc: 30 mg/day, in combination with other natural health product ingredients (Segger & Schonlau, 2004) Zinc: 5 mg/day, in combination with other natural health product ingredients (Skovgaard et al. 2006) Zinc: 45 mg/day (Prasad et al. 2004) Zinc: 30 mg/day (Roussel et al. 2003) |
| Selenium | 3.5 mcg | 400 mcg | Selenium: 3.5-400 mcg/day (NHPD monograph: selenium) Selenium: 75 mcg/day, in combination with other natural health product ingredients (Heinrich et al. 2006) Selenium in combination with other natural health product ingredients (Greul et al. 2002) |
| Cat's Claw Extract (bark) (*Uncaria Tomentosa*) [8% Carboxy Alkyl Esters] | 100 mg | 400 mg | Cat's claw extract (C-MED-100): 250 or 350 mg/day (Sheng et al. 2001) Cat's claw extract (C-MED-100): 400 mg/day, in combination with other natural health |

TABLE 3-continued

| Medicinal Ingredients | Minimum dose per day | Maximum dose per day | References |
|---|---|---|---|
| Phytosterol Extract (*glycine max*) [40% Beta-sitosterol] | 100 mg | 400 mg | product ingredients (Pero et al. 2005) No recommendations for human dosing. |
| Japanese Knotweed Extract (root) (*Polygonum cuspidatum*) [50% Resveratrol] | 25 mg | 200 mg | Grape juice: 10 mL/kg body weight/day (O'Byrne et al. 2002) |
| Beta-alanine | 50 mg | 500 mg | Beta-alanine: 3.2 or 6.4 g/day (Harris et al. 2006; Stout et al. 2007; Stout et al. 2006) Beta-alanine: 4.0-6.4 g/day (Hill et al. 2007) |
| Forskohlii Extract (root) [40% Forskohlin] | 31.25 mg | 125 mg | Forskohlin: 50 mg/day (Sabinsa, 2000; Godard et al. 2005) |
| Caffeine | 0 mg | 150 mg | Caffeine: 100 mg/day (Dulloo et al. 1989) Caffeine: 5 mg/kg fat free mass (Arciero et al. 2000) Caffeine: 100, 200 and 400 mg/day (Astrup et al. 1990) |
| Green Tea Extract (leaf) [98% Polyphenols, 80% Catechins, 45% EGCG] | 200 mg | 1000 mg | Green tea: 2 cups/day, providing 250 mg/day of catechins) (Erba et al. 2005) Catechins: 690 mg/day (Nagao et al. 2005) EGCG: 270 mg/day (Chantre & Lairon, 2002) EGCG: 270 mg/day (Dulloo et al. 1999) EGCG: 270 mg/day in combination with Caffeine (600 mg/day) (Berube-Parent et al. 2005) EGCG: 270 mg/day in combination with Caffeine (150 mg/day) (Westerterp-Plantenga et al. 2005) |
| Astaxanthin Extract (*Haematocuccus pluvialis* [2% astaxanthin] | 100 mg | 1000 mg | Astaxanthin: 4 mg, twice daily (Karppi et al. 2007) Astaxanthin: 2 mg, twice daily (Yamashita, 2006) |
| *Rhodiola* Extract (root) [3% Rosavins, 1% Salidrosides] | 50 mg | 500 mg | *Rhodiola* extract: 100 mg/day containing 3% (3 mg/day) of rosavins (Spasov et al. 2000) |

The cantaloupe melon extract standardized for superoxide dismutase may be provided in a daily dosage of about 100 mg to about 900 mg.

In another aspect, the present invention is a method for promoting internal health and external appearance in a subject, said method comprising administering to the subject a composition comprising resveratrol, forskohlin and astaxanthin. In another aspect of the method of the present invention the composition comprises resveratrol, forskohlin, astaxanthin, carboxy alkyl ester and superoxide dismutase.

In one aspect the present invention comprises a method for promoting internal health and external appearance in a subject, said method comprising administering to the subject a composition comprising: carboxy alkyl ester, beta-sitosterol, resveratrol, beta-alanine, forskohlin, a neuroprotectan, epigallocatechin-gallate (EGCG), astaxanthin, rosavins and salidrosides.

The term "subject" as used herein includes all members of the animal kingdom including humans. The subject is preferably a human.

Compositions according to the present invention may be readily prepared according to standard procedures known in the art for the preparation of compositions for oral administration. Capsules may contain colorants such as a chlorophyliin copper complex, which serves as a colouring agent for the capsule shell.

Extracts of may be prepared according to standard procedures known in the art for the preparation of plant extracts. Extracts, amino acid, vitamins, minerals and caffeine may also be obtained from commercial sources ready to be blend into the compositions of the present invention from a variety of commercial suppliers.

Each one of the components of the present invention functions in the support of one or more of enhancing DNA repair, helping reduce body fat levels and preserve lean body mass, promoting skin health or helping reduce the appearance of wrinkles in a subject in need, and will therefore be discussed in multiple contexts.

*Uncaria tomentosa* (bark), *Indian colchicum* (root), and *Haematococcus pluvialis* (microalgae) have been chosen based on their ability to control the three major causes of human ageing: DNA degradation at the cellular level, sarcopenia at the muscular level, and Singlet Oxygen Species (SOS) Free-Radical Damage at the skin surface cell membrane level. *Uncaria tomentosa* (bark) [standardized for carboxy alkyl ester] has been shown in human clinical research to increase DNA repair after DNA damage was induced (Sheng Y., et al. (2001)). *Indian Colchicum* (root) [standardized for colforsin] has been shown in human clinical research to reduce body fat levels while maintaining lean body tissue in sedentary human subjects (Godard M., et al. (2005)). *Haematococcus pluvialis* (microalgae) [standardized for astaxanthin] has been shown in human clinical research to decrease wrinkle appearance, improve skin elasticity and increase skin moisture by neutralizing the Singlet Oxygen Species Free-Radical at the cellular membrane level (Yamashita E., et al. (2006); Nashita Y., et al. (2007); NcNulty H., et al. (2007)).

NU-100™ also includes *Polygonum cuspidatum* (root), and *Glycine max* (seed). These compounds have been chosen based on their ability to increase DNA repair in humans and improve healthy gene expression. *Polygonum cuspidatum* (root) has been included based on its ability to activate the SIR1 enzyme in the human body. This enzyme helps lengthen the life span of human cells by maintaining chromosomal telomere length in human cells. This helps to increase the number of times a cell can replicate in a healthy disease-free manner.

NU-100™ also includes beta-alanine, and caffeine. These compounds have been chosen based on their ability to reduce body fat levels in humans, prevent muscle tissue loss and increase skin firmness.

NU-100™ also includes *Camellia sinensis* (leaf), *Haematococcus pluvialis* (micoralgae), and *Rhodiola rosea* (root). These compounds have been chosen based on their direct and indirect ability to improve skin surface health by reducing appearance of wrinkles, increasing skin elasticity and increasing skin moisture while protecting skin from UV photo damage.

*Camellia sinensis* (Green Tea)

In one aspect of the present invention, *Camellia sinensis* (leaf, green tea) is included as an extract standardized to about 98% polyphenols, 80% catechins, 45% epigallocatechin-3-gallate (EGCG). Research indicates that EGCG protects the skin from UV damage from the sun. EGCG has been identified as the most potent and most important photoprotective (skin protection) polyphenolic component in green tea.

In one aspect, the green tea extract is between 35% and 36% of the total composition of NU-100™. In another aspect, the *Camellia sinensis* extract is 35.39% of the total composition of NU-100™.

In one aspect of the composition of the present invention the composition comprises a daily dose of from about 200 mg to 1000 mg of green tea extract. In another aspect the composition of the invention comprises a daily dose of from about 400 mg to 800 mg of green tea extract. In yet another aspect, the composition of the invention comprises a daily dose of 602 mg of green tea extract.

Green tea extract is commercially available. For example as an extract standard: 98% polyphenols/80% [210 mg] catechins/45% [135 mg] EGCG (Naturex, South Hackensack-N.J. 07606).

As previously mentioned, and also discussed in a recent review by Katiyar et al. (2007), human skin is constantly exposed to numerous physical, chemical and environmental stressors, some of which directly or indirectly adversely affect the skin. Cutaneous overexposure to environmental solar ultraviolet (UV) radiation has a variety of adverse effects on human health, including the development of melanoma and nonmelanoma skin cancers. Environmental pollutants and UV light are also key factors that contribute to the structural damage of the skin's vital components, and the resultant appearance of fine lines and wrinkles. Katiyar and colleagues discuss that the polyphenols present in green tea have been shown to have numerous health benefits, including protection from UV carcinogenesis, identifying EGCG as the major and most photoprotective polyphenolic component of green tea. They report in their review of green tea research that the oral administration of green tea polyphenols in drinking water or the topical application of EGCG prevents UVB-induced skin tumor development in mice, and this prevention is mediated through numerous mechanisms, including the induction of immunoregulatory cytokines, DNA repair, the inhibition of UV-induced immunosuppression through cytokine-dependent DNA repair, the inhibition of angiogenic factors, and the stimulation of cytotoxic T cells in a tumor microenvironment (Katiyar et al. 2007).

Green tea's antioxidant properties have been demonstrated in vitro and in clinical studies. For example, free radical scavenging activity of green tea polyphenols and catechins has been shown in assays measuring antioxidant capacity by Seeram et al. (2006) and Henning et al. (2003). Additionally, the results of a randomized, controlled trial in women conducted by Erba (2005) have shown that supplementation with green tea (consumed with a balanced diet) can improve overall antioxidant status, and protect against oxidative damage. Findings showed that green tea supplementation resulted in a significant increase in plasma total antioxidant activity and a significant decrease in plasma peroxidase levels and oxidative DNA damage (Erba, 2005).

Green tea has been shown to have an effect on increasing fat oxidation and metabolism. By helping to decrease body fat mass, green tea can inadvertently shift the body ratio of fat mass to lean mass in a favourable way. Green tea has been studied for its effects on fat oxidation and thermogenesis in a variety of research models, including in vitro, animal and clinical trials. In a recent review by Wolfram et al. (2006), the authors commented that the anti-obesity effects of green tea are being increasingly investigated in cell, animal, and human studies. Green tea, green tea catechins, and epigallocatechin gallate (EGCG) have been demonstrated in cell culture and animal models of obesity to reduce adipocyte differentiation and proliferation, lipogenesis, fat mass, body weight, fat absorption, plasma levels of triglycerides, free fatty acids, cholesterol, glucose, insulin and leptin, as well as to increase beta-oxidation and thermogenesis. Adipose tissue, liver, intestine, and skeletal muscle are target organs of green tea, mediating its anti-obesity effects. Studies conducted with human subjects report reduced body weight and body fat, as well as increased fat oxidation and thermogenesis and thereby confirm findings in cell culture systems and animal models of obesity (Wolfram et al. 2006).

The findings of a double blind, placebo-controlled human trial showed that treatment with green tea supplementation resulted in a significant decrease in both total and subcutaneous abdominal fat area, as well as waist circumference and skin-fold thickness following 12 weeks of treatment (Nagao et al. 2005). Chantre & Lairon (2002) found that a green tea extract exerts a direct inhibition of gastric and pancreatic lipases and a stimulation of thermogenesis. In their open study, moderately obese patients decreased their body weight by 4.6% and waist circumference by 4.48%, following 3 months of supplementation. Dulloo et al. (1999) concluded that oral administration of green tea extract to healthy men stimulated thermogenesis and fat oxidation and thus has the potential to influence body weight and body composition via changes in both energy expenditure and substrate utilization. Berube-Parent et al. (2005) conducted a double-blind, placebo-controlled study, in which they found that green tea extract increased the 24 hour energy expenditure of 14 subjects. Westerterp-Plantega et al. (2005) administered a green tea-caffeine mixture or placebo to 76 subjects, and found that in habitual low caffeine consumers, the green tea-caffeine mixture improved weight maintenance, partly through thermogenesis and fat oxidation.

In animal studies, Choo (2003) observed that green tea inhibited the increase in body fat content caused by feeding a high-fat diet in rats. There was no effect on energy intake and this body fat-suppressive effect of green tea resulted in part from reduction in digestibility and to much greater extent from increase in brown adipose tissue thermogenesis through beta-adrenoceptor activation. Dulloo et al. (2000) reported from their in vitro study that green tea extract stimulates brown adipose tissue thermogenesis to an extent which is much greater than can be attributed to its caffeine content per se, and that its thermogenic properties could reside primarily in an interaction between its high content in catechin-polyphenols and caffeine with sympathetically released noradrenaline (NA).

*Uncaria tomentosa* (Cat's Claw)

In one aspect, *Uncaria tomentosa* is included as an extract standardized to about 8% carboxy alkyl esters content. Carboxy alkyl esters promotes DNA repair in mammals, such as humans. In another aspect, the *Uncaria tomentosa* extract is between 14% and 15% of the total composition of NU-100™. In yet another aspect, the *Uncaria tomentosa* extract is 14.69% of the total composition of NU-100™.

In one aspect of the present invention, the composition comprises a daily dose of from about 100 mg to 400 mg of *Uncaria tomentosa* extract. In another aspect the composition of the invention comprises a daily dose of from about 150 mg to 300 mg of *Uncaria tomentosa* extract. In yet another aspect, the composition of the invention comprises a daily dose of 250 mg of *Uncaria tomentosa* extract.

*Uncaria tomentosa* is commercially available, for example as AC-11® Certified Authentic Brazilian Cat's Claw Extract (*Uncaria tomentosa*) (bark) standardized to 8% (10 mg) carboxy alkyl esters (Optigenex Inc, New York, N.Y. 10022).

Cat's claw can help combat reactive oxygen species due to its antioxidant properties, and therefore minimize the damage to DNA that may have otherwise been inflicted. The antioxidant properties of cat's claw have been demonstrated in many in vitro studies. Recently, Pilarski et al. (2006) evaluated the antioxidant properties of aqueous and ethanolic extracts of cat's claw; their analysis included trolox equivalent antioxidant capacity (TEAC), peroxyl radical-trapping capacity (PRTC), superoxide radical scavenging activity (SOD) and quantitation of total tannins (TT) and total phenolic compounds (TPC). The obtained results indicated high antioxidant capacity of the studied materials in comparison to other extracts of fruits, vegetables, cereals and medicinal plants. It was also shown that the ethanolic extract exhibited stronger antioxidant activity than the aqueous extract.

The ability of cat's claw to minimize or inhibit DNA mutation or promote DNA repair has been demonstrated in in vitro, animal and human trials. Mammone et al. (2006) investigated the ability of cat's claw to promote DNA repair in primary organ cultures of human skin. Skin cultures were treated with or without 5 mg/mL of a standardized cat's claw extract and irradiated with 0-100 mJ/cm2 UVB, following which they were microscopically analyzed for necrosis as well as the level of pyrimidine dimers using immunofluorescent TT-dimer antibody staining. The data clearly demonstrated that co-incubation with cat's claw reduced skin cell death from UV exposure, and this protection was accounted for by a concomitant increase in DNA repair (Mammone et al. 2006). Cat's claw extract has also been shown to be an effective DNA repair agent in rats. In a study by Sheng et al. (2000), repair of DNA single strand breaks (SSB) and double strand breaks (DSB) 3 hours after whole body irradiation of rats was significantly improved in animals supplemented with a standardized cat's claw extract compared to controls (Sheng et al. 2000).

Positive results have also been obtained in studies conducted in humans. In a trial conducted by Sheng et al. (2001), healthy adults were supplemented with two different doses of a standardized cat's claw extract or placebo for 8 weeks. DNA repair after induction of DNA damage by a standard dose of hydrogen peroxide was measured 3 times before supplement administration and 3 times after supplement administration for the last 3 weeks of the 8 week-supplement period. The results indicated that there was a statistically significant decrease of DNA damage and a concomitant increase of DNA repair in the supplement groups (250 and 350 mg/day) when compared with non-supplemented controls (Sheng et al. 2001). Furthermore, cat's claw supplementation in combination with other nutritional supplements has also demonstrated efficacy in enhancing DNA repair in a more recent clinical trail. Pero et al. (2005) found that supplementation with cat's claw in combination with mushroom extracts, nicotinamide and zinc for 4 weeks resulted in a reduced presence of DNA damage in peripheral blood assessed by (8-OH) guanine DNA adducts (Pero et al. 2005).

*Haematococcus Pluvialis*

In one aspect of the present invention, *Haematococcus pluvialis* (microalgae) is included as an extract to 2% astaxanthin content. Astaxanthin is a powerful antioxidant that helps to neutralize the singlet-oxygen-species (SOS) free radicals. SOS is the most dangerous free-radical in the body that directly damages the epidermal layer of the skin and destroys health cellular membrane function. In one aspect, the *Haematococcus pluvialis* (microalgae) extract is between 11% and 12% of the total composition of NU-100™. In another aspect, *Haematococcus pluvialis* (microalgae) extract is 11.75% of the total composition of NU-100™.

In one aspect of the composition of the present invention the composition comprises a daily dose of from about 100 mg to 1000 mg of *Haematococcus pluvialis* extract. In another aspect the composition of the invention comprises a daily dose of from about 100 mg to 600 mg of *Haematococcus pluvialis* extract. In yet another aspect, the composition of the invention comprises a daily dose of 200 mg of *Haematococcus pluvialis* extract.

Oxidative stress is the main contributor to photo-ageing, which results in the formation on visible lines and wrinkles in the skin. Astaxanthin's antioxidant properties can help fight singlet oxygen species free radicals and help reduce the effects of photo-ageing, promoting improved skin health and appearance. As discussed in a recent review by Hussein et al. (2006), astaxanthin is a powerful biological antioxidant with considerable potential and promising applications in human health and nutrition.

Astaxanthin's antioxidant properties have been studied in vitro and in clinical settings. O'Connor & O'Brien (1998) evaluated the ability of astaxanthin to protect against UVA-induced oxidative stress in an in vitro model using rat kidney fibroblasts. Activities of the antioxidant enzymes catalase (CAT) and superoxide dismutase (SOD), and changes in thiobarbituric acid reactive substances (TBARS) were measured as indices of oxidative stress. Exposure to UVA light resulted in a significant decrease in CAT and SOD activities and a significant increase in TBARS; astaxanthin was found to inhibit these indices of oxidative stress, also exhibiting superior protective properties compared to beta-carotene and lutein (O'Connor & O'Brien, 1998).

To investigate the antioxidant effects of astaxanthin in humans, Karppi et al. (2007) conducted a randomized, double-blind, placebo-controlled study investigating the ability of astaxanthin to protect against lipid peroxidation. Results showed that astaxanthin supplementation significantly elevated plasma astaxanthin levels. It was observed that levels of plasma 12- and 15-hydroxy fatty acids were reduced significantly in the astaxanthin group during supplementation, but not in the placebo group and the change of 15-hydroxy fatty acid was almost significantly greater in the astaxanthin group, as compared with the placebo group. The authors concluded that intestinal absorption of astaxanthin delivered as capsules is adequate and well tolerated, and that supplementation with astaxanthin may decrease in vivo oxidation of fatty acids in healthy subjects (Karppi et al. 2007).

Furthermore, the results of a clinical trial by Hashimoto (2006) directly demonstrate the effects of astaxanthin supplementation on skin appearance. In their study, middle-aged women were assigned to supplementation with astaxanthin or placebo for of six weeks, following which an evaluation of skin characteristics took place. Measurement parameters included a questionnaire, inspection by a dermatologist, determination of skin moisture content and elasticity, as well as observation of the skin surface with photographs. Results indicated that there were significant improvements in fine lines and wrinkles as well as elasticity and moisture content, as assessed by instrumentation and by the dermatologist's review (Yamashita, 2006).

*Glycine Max*

In one aspect, *glycine max* (seed) is included as an extract standardized to 84% phytosterols (including B-sitosterols, campesterol, stigmasterol) content. Phytosterols support healthy immune function by preventing cholesterol oxidation and the associated inflammation and immune system dysfunction this causes. Inflammation is the root cause of all disease and disorder and phytosterols inhibit that absorption and metabolism of cholesterol helping to naturally protect the vascular system, heart and cellular DNA from inflammation and free-radical production. In some aspect, the *glycine max* (seed) extract is between 8% and 9% of the total composition of NU-100™. In a yet another aspect, *glycine max* (seed) extract is 8.81% of the total composition of NU-100™.

In one aspect of the composition of the present invention the composition comprises a daily dose of from about 100 mg to 400 mg of *glycine max* extract. In another aspect the composition of the invention comprises a daily dose of from about 100 mg to 300 mg of *glycine max* extract. In yet another aspect, the composition of the invention comprises a daily dose of 150 mg of *glycine max* extract.

Beta-sitosterol has antioxidant potential, and can therefore help reduced oxidative stress and subsequent damage to cellular components, such as DNA.

Several in vitro studies have demonstrated the antioxidant potential of beta-sitosterol. For example, the results of an in vitro trial by Yoshida et al. (2003) demonstrated that beta-sitosterol chemically acts as an antioxidant, a modest radical scavenger, and physically as a stabilizer in membranes. In addition, Vivancos & Moreno (2005) showed that beta-sitosterol reverts the impairment of the glutathione/oxidized glutathione ratio induced by phorbol esters in macrophage cultures. Direct protective effects on DNA have also been demonstrated. Most recently, Li et al. (2007) set out to determine the effect of beta-sitosterol on early cellular damage in irradiated thymocytes. In their study, thymocytes were irradiated (6 Gy) with or without beta-sitosterol and cell apoptosis and apoptosis-related proteins were evaluated. Results indicated that beta-sitosterol decreased irradiation-induced cell death and nuclear DNA strand breaks, while attenuating intracellular reactive oxygen species (ROS) and increasing the activities of antioxidant enzymes, including superoxide dismutase (SOD), catalase (CAT), and glutathione peroxidase (GPx) (Li et al. 2007).

*Polygonum cuspidatum* (Japanese Knotweed)

In one aspect, *Polygonum cuspidatum* (root) is included as an extract standardized to 50% trans-resveratrol content. In some aspect, the *Polygonum cuspidatum* (root) extract is between 5% and 6% of the total composition of NU-100™. In another aspect, *Polygonum cuspidatum* (root) extract is 5.87% of the total composition of NU-100™.

In one aspect of the composition of the present invention the composition comprises a daily dose of from about 25 mg to 200 mg of *Polygonum cuspidatum* extract. In another aspect the composition of the invention comprises a daily dose of from about 50 mg to 150 mg of *Polygonum cuspidatum* extract. In yet another aspect, the composition of the invention comprises a daily dose of 100 mg of *Polygonum cuspidatum* extract.

Trans-resveratrol, which may also be derived from wine and grapes, is a polyphenolic compound, which has demonstrated antioxidant potential in a number of research systems. For example, resveratrol has been shown to reduce oxidative stress induced by platinum compounds in human plasma, blood platelets and lymphocytes in vitro (Olas et al. 2005). Olas et al. (2005) found that resveratrol decreased the production of a biomarker of lipid peroxidation in control blood platelets and platelets treated with platinum compounds, and markedly reduced activities of different anti-oxidative enzymes in these cells. Resveratrol also evoked a significant decrease of DNA damage (measured by comet assay) in lymphocytes compared with cells treated with platinum compounds without resveratrol. Additionally, resveratrol also caused a distinct reduction of oxidative stress levles in plasma after incubation with platinum compounds. The authors concluded that the antioxidative activity of resveratrol may diminish oxidative stress and damage to cellular biomolecules (lipids, proteins and DNA) induced by platinum compounds (Olas et al. 2005). Resveratrol has also exhibited antioxidant activity in animal studies. Kumar et al. (2007) found that intraperitoneal treatment with resveratrol for 2 weeks in a rat model of diabetic neuropathy resulted in protective effects on several pathologies associated with diabetic neuropathy, which the authors concluded were likely mediated through a reduction in oxidative stress and DNA fragmentation.

In humans, the effects of supplementation with grape products have been investigated on antioxidant capacity and oxidative stress. As grapes are the most widely recognized sources of resveratrol, beneficial effects observed from grape supplementation, may be at least in part, attributed to their naturally occurring resveratrol content. O'Byrne et al. (2002) found that supplementation of healthy adults with concord grape juice increased serum antioxidant capacity and protected LDL against oxidation to an extent similar to that obtained with alpha-tocopherol supplementation, but decreased native plasma protein oxidation significantly more than alpha-tocopherol did.

Indian colchicum

In one aspect the composition of the invention includes a daily dose of *Indian colchicum* extract. In another aspect of the present invention, *Indian colchicum* (root) is included as an extract standardized to 40% forskohliin. Forskohliin (colforsin) is a safe breakthrough new phytocompound that significantly reduces body fat levels, prevents loss of muscle and firms up the appearance of skin. This compound works to naturally stimulate adenylate cyclase and cyclic AMP levels. This is the key driver that activates hormone sensitive lipase (HSL) which causes the breakdown and release of stored body fat. Colforsin has been shown in human clinical research to reduce body fat levels while maintaining lean body tissue in sedentary human subjects (Godard et al. 2005).

In one aspect, the *Indian colchicum* (root) extract is between 7% and 8% of the total composition of NU-100™. In another aspect, *Indian colchicum* (root) extract is 7.34% of the total composition of NU-100™.

In one aspect of the composition of the present invention the composition comprises a daily dose of from about 25 mg to 200 mg of *Indian colchicum* extract. In another aspect the composition of the invention comprises a daily dose of from about 50 mg to 150 mg of *Indian colchicum* extract. In yet another aspect, the composition of the invention comprises a daily dose of 125 mg of *Indian colchicum* extract standardized to 40% forskohlin.

It has been demonstrated in clinical research that *Coleus forskohlii* extract helps promote lean body mass development, while working to decrease fat accumulation. In a human study conducted by a manufacturer of a patented *Coleus forskohlii* material, it was demonstrated that volunteers treated with forskohlii extract lost significantly more weight and gained significantly more lean body mass compared to placebo (Sabina Corporation, 2000). In a study by Godard et al. (2005), forkohlin supplementation was also shown to favorably affect body composition by decreasing body fat percentage and body fat mass. Additionally, there was a statistically significant change in the group receiving forskohlin from pre to post supplementation values for lean body mass; it was observed that subjects in the forkohlin group, on average, gained 8.2 pounds of lean body mass in the course of the study. This finding resulted in a trend toward significance for lean body mass between the forskohlin group and placebo, as the placebo group also gained some lean body mass, although to a lesser extent, over the course of the study (Godard et al. 2005).

*Rhodiola rosea*

In one aspect of the present invention the composition of the invention includes a daily dose of *Rhodiola rosea* extract. In another aspect of the present invention, *Rhodiola rosea* (root) is included as an extract standardized to 3% rosavins and 1% salidrosides. Rosavins and salidrosides have been included to counterbalance the stimulatory effects (i.e. anxiety, jitteriness, etc.) that some individuals may experience due to caffeine intake.

In one aspect, the *Rhodiola rosea* (root) extract is between 5% and 6% of the total composition of NU-100™. In another aspect, *Rhodiola rosea* (root) extract is 5.87% of the total composition of NU-100™.

In one aspect of the composition of the present invention the composition comprises a daily dose of from about 50 mg to 500 mg of *Rhodiola rosea* extract. In another aspect the composition of the invention comprises a daily dose of from about 75 mg to 250 mg of *Rhodiola rosea* extract. In a yet another aspect, the composition of the invention comprises a daily dose of 100 mg of *Rhodiola rosea* extract.

*Rhodiola* has been shown to be effective in reducing stress in clinical research. As outlined in a review by Kelly (2001), *rhodiola* has been well characterized as an adaptogen due to its observed ability to increase resistance to a variety of chemical, biological and physical stressors. The findings of a randomized, double-blind, placebo-controlled human trial revealed that treatment with *rhodiola* for 20 days resulted in decreased mental fatigue and situational anxiety in university aged (17-19 years) students (Spasov et al. 2000).

Caffeine

In one aspect the composition of the invention includes a daily dose of caffeine.

In one aspect, the caffeine is between 4% and 5% of the total composition of NU-100™. In a preferred aspect, caffeine is 4.41% of the total composition of NU-100™.

In another aspect of the composition of the present invention the composition comprises a daily dose of from about 1 mg to 150 mg of caffeine. In another aspect the composition of the invention comprises a daily dose of from about 25 mg to 100 mg of caffeine. In yet another aspect, the composition of the invention comprises a daily dose of 75 mg of caffeine.

Caffeine has been included in the AGEOFF formulation to support the product's claim to preserve lean body mass. Caffeine can positively influence the body's fat mass to lean mass ratio by promoting fat oxidation and increasing thermogenesis. Caffeine is a compound that exists naturally in certain plants, but can also be produced synthetically and used as an additive in food or supplement products. Its effects on the central nervous system and thermogenesis can help contribute to fat breakdown and fat loss. A review by Westerterp-Plantenga et al. (2006) discusses that functional ingredients, such as caffeine, have the potential to produce significant effects on metabolic targets such as satiety, thermogenesis, and fat oxidation. Such thermogenic ingredients may be considered as functional agents that could help in preventing a positive energy balance and obesity (Westerterp-Plantenga et al. 2006).

A randomized controlled trial completed by Dulloo et al. (1989) showed results where measurements of energy expenditure (EE) in a room respirometer indicated that repeated caffeine administration at 2-hour intervals over a 12-hour day period increased the EE of two subject groups by 8-11%, but had no influence on the subsequent 12-h night EE. The net effect was a significant increase in daily EE of 150 kcal in the lean volunteers and 79 kcal in the post-obese subjects. It was concluded that caffeine at commonly consumed doses can have a significant influence on energy balance and may promote thermogenesis in the treatment of obesity. In addition, it was concluded in a randomized controlled trial by Arciero et al. (2000) that older and younger women increased energy expenditure significantly following caffeine ingestion, although older women had a blunted thermic response compared with younger women. The thermic response to caffeine was positively associated with body weight and waist circumference in younger women, whereas a positive association with aerobic fitness was observed in older women. In another randomized trial by Arciero et al. (1995), it was concluded that older and younger men show a similar thermogenic response to caffeine ingestion, whereas older men show a smaller increase in fatty acid availability after a caffeine challenge. The results of a clinical supplementation study with caffeine conducted by Astrup et al. (1990) showed that caffeine increased energy expenditure dose dependently and the thermogenic response was positively correlated with the response in plasma caffeine.

In addition to its effects on lean body composition, caffeine also has neuroprotective effects due to its adenosine A(2A) receptor antagonist activity. During the last decade, the adenosine A(2A) receptor has emerged as an attractive target for Parkinson's disease therapy, primarily because of its localized expression in striatum and motor enhancement function (Chen, 2003). In fact, large prospective epidemiologic studies have linked the consumption of coffee and other caffeinated beverages to a reduced risk of subsequently developing Parkinson's disease. Most recently, Hu et al. 2007 examined the association of coffee and tea consumption with the risk of incident Parkinson's disease among 29,335 Finnish subjects aged 25 to 74 years without a history of Parkinson's disease at baseline. During a mean follow-up of 12.9 years, 102 men and 98 women developed Parkinson's. The multivariate-adjusted hazard ratios of Parkinson's disease associated with the amount of coffee consumed daily (0, 1-4, and >/=5 cups) were 1.00, 0.55, and 0.41 in men, 1.00, 0.50, and 0.39 in women, and 1.00, 0.53, and 0.40 in men and women combined (adjusted also for sex), respectively. These authors suggested that coffee drinking is associated with a lower risk of Parkinson's disease (Hu et al. 2007). Furthermore, the results of a study by Joghataie et al. (2004) showed protective effects of caffeine against neurodegeneration in a model of Parkinson's disease in rats.

Beta-Alanine

In one aspect the composition of the invention includes a daily dose of Beta-alanine. Beta-alanine has been shown to prevent muscle loss and support lean body composition.

In one aspect, the Beta-alanine is between 5% and 6% of the total composition of NU-100™. In another aspect of the present invention, Beta-alanine is 5.87% of the total composition of NU-100™.

In one aspect of the composition of the present invention the composition comprises a daily dose of from about 50 mg to 500 mg of Beta-alanine. In another aspect the composition of the invention comprises a daily dose of from about 75 mg to 250 mg of Beta-alanine. In yet another aspect, the composition of the invention comprises a daily dose of 100 mg of Beta-alanine.

Several clinical studies have investigated the effects of beta-alanine on muscle physiology, strength and performance. Harris et al. (2006) found that supplementation with beta-alanine resulted in significant increases in muscle carnosine levels in the vastus lateralis. This is an important finding as various physiological actions have been ascribed to carnosine content in muscle, including pH buffering. As intense exercise results in the accumulation of lactate and H+, decreases in muscle pH are thought to play a role in fatigue (Harris et al. 2006). Stout et al. (2007) examined the effects of beta-alanine supplementation over a period of 4 weeks on the fatigue and ventilatory threshold in women subjects. Their findings indicated that beta-alanine supplementation delayed the onset of neuromuscular fatigue and the ventilatory threshold at submaximal workloads, and increased the time-to-exhaustion during maximal cycle ergometry performance (Stout et al. 2007). In male subjects, Hill et al. (2007) found that supplementation with beta-alanine resulted in significant muscle carnosine level increases, as well as an increase in total work done as evaluated by cycling capacity.

Additionally, Stout et al. (2006) conducted a randomized, double-blind, placebo controlled study examining the effect of 28 days of beta-alanine supplementation (with and without additional creatine) on neuromuscular fatigue by using the measurement of physical working capacity at neuromuscular fatigue threshold (PWCFT). Subjects performed a continuous incremental cycle ergometer test before and after the 28 day supplementation period during which a surface electromyographic signal was recorded from the vastus lateralis muscle to determine PWCFT. Results showed that 28 days of beta-alanine supplementation resulted in a statistically significant increase in PWCFT of 14.5% (Stout et al. 2006). The increase in PWCFT, as found by Stout et al. (2006), reflects an enhanced capacity of the muscle to perform a specific task at a defined intensity, and thus can be interpreted as increase in muscle power.

Superoxide Dismutase

In one aspect the composition of the invention includes a daily dose of a superoxide dismutase extract.

In one aspect of the composition of the present invention the composition comprises a daily dose of from about 100 mg to 900 mg of cantaloupe melon extract standardized for superoxide dismutase.

Superoxide dismutase is a major cytoplasmic antioxidant enzyme that metabolizes superoxide radicals to molecular oxygen and hydrogen peroxide, thus providing a defense against oxygen toxicity (Niwa et al., 2007). Pretreatment of pigs with superoxide dismutase, protected against DNA strand-break damage induced by hyperbaric oxygen (HBO) (Albacini et al., 2005).

Vitamin C

In one aspect the composition of the invention includes a daily dose of vitamin C.

In one aspect, the vitamin C is between 25% and 26% of the total vitamin/mineral composition of the composition of this invention. In another a spect, vitamin C is 25.79% of the vitamin/mineral composition of the composition of the present invention.

In one aspect of the composition of the present invention the composition of the present invention comprises a daily dose of about 6 mg to 2000 mg of vitamin C. In another aspect the composition of the present invention comprises a daily dose of 60 mg of vitamin C.

Vitamin C promotes internal health, as well as helps improve the health and appearance of skin. The NHPD has approved the use of vitamin C as an antioxidant for the maintenance of good health (NHPD monograph: vitamin C). Furthermore, its antioxidant activity can also have a beneficial effect on outward appearance or external beauty. As discussed by Flora (2007), antioxidants are intimately involved in the prevention of cellular damage—the common pathway for ageing and numerous diseases. These molecules safely interact with free radicals and terminate the free radical chain reaction before vital molecules are damaged. It has been shown that levels of ascorbic acid in the skin can become depleted with ageing. In fact, Leveque et al. (2003) found that there is a direct relationship between ascorbic acid concentrations in the dermis and ageing. In their observational study, they showed that an inverse correlation between ascorbic acid dermis levels and increasing age exists (Leveque et al. 2003). Furthermore, in their review of the antioxidant network of the stratum corneum, Thiele et al. (2001) presented data suggesting that under conditions of oxidative stress, topical and/or systemic application of antioxidants could support physiological mechanisms to maintain or restore a healthy skin barrier.

In support of these findings, Mireles-Rocha et al. (2002) showed that the median minimal erythema dose of subjects supplemented with vitamin C and vitamin E significantly increased from 50 to 70 mJ/cm2 compared to placebo, demonstrating a photo-protective effect against ultraviolet (UV) radiation. Additionally, a protective effect against sunburn of combined systemic ascorbic acid and d-alpha-tocopherol supplementation was also demonstrated in a clinical trial by Eberlein-König et al. (1998). Therefore, supplementation with vitamin C can not only contribute to maintenance of overall health and well-being, but it can also exert a positive effect on outward appearance, by helping to minimize oxidative damage to skin tissue.

Vitamin D

In one aspect the composition of the invention includes a daily dose of vitamin D.

In one aspect, the vitamin D is between 2.0% and 3.5% of the vitamin/mineral composition of the composition of this invention. In another aspect, vitamin D is 2.82% of the vitamin/mineral composition of the composition of the present invention.

In one aspect of the present invention the composition comprises a daily dose of about 32 IU to 1000 IU of vitamin D. In another aspect, the composition of the present invention comprises 800 IU of vitamin D.

Vitamin D promotes internal health. The NHPD has approved the use of vitamin D for the maintenance of good health (NHPD monograph: vitamin D).

Vitamin E

In one aspect the composition of the invention includes a daily dose of vitamin E.

In one aspect, the vitamin E is between 13% and 14% of the vitamin/mineral composition of the composition of this invention. In another aspect, vitamin E is 13.84% of the vitamin/mineral composition of the composition of the present invention.

In one aspect of the composition of the present invention, the composition of the present invention comprises a daily dose of about 10 IU to 400 IU of vitamin E. In another aspect, the composition of the present invention comprises 30 IU of vitamin E.

Vitamin E promotes internal health, help improve the health and appearance of skin, and also promote DNA repair. The antioxidant properties of vitamin E help combat oxidative stress, which is implicated in the ageing process and many degenerative diseases. As explained by Nachbar & Korting (1995), the skin is exposed to numerous environmental, chemical and physical agents such as ultraviolet light, causing oxidative stress. This results in several short- and long-term adverse effects such as erythema, edema, skin thickening, wrinkling, and an increased incidence of skin cancer or precursor lesions. Accelerated cutaneous ageing under the influence of ultraviolet light, usually termed photoageing, is only one of the harmful effects of continual oxygen radical production in the skin. Vitamin E is the major naturally occurring lipid-soluble non-enzymatic antioxidant protecting skin from the adverse effects of oxidative stress including photoageing. Many studies document that vitamin E occupies a central position as a highly efficient antioxidant, thereby providing possibilities to decrease the frequency and severity of pathological events in the skin (Nackbar & Korting, 1995). In fact, Thiele et al. (2001) discuss that alpha-tocopherol depletion is a very early and sensitive biomarker of environmentally induced oxidation.

Supplementation with vitamin E can therefore help mitigate the adverse effects of oxidative stress on the body, and in turn promote improved skin appearance and better overall health. In fact, Cadenas et al. (1996) demonstrated the benefits of vitamin E supplementation in healthy human volunteers on markers of endogenous oxidative stress. They found that the urine of subjects supplemented with vitamin E showed significantly and progressively smaller lipid peroxidation products as supplementation progressed, reaching a 27% decrease at the end of the treatment period. The authors concluded that dietary doses of vitamin E are able to decrease endogenous oxidative stress in healthy humans routinely performing their normal activities (Cadenas et al. 1996). As previously mentioned, Mireles-Rocha et al. (2002) showed that the median minimal erythema dose of subjects supplemented with vitamin C and vitamin E significantly increased from 50 to 70 mJ/cm2 compared to placebo, demonstrating a photo-protective effect against ultraviolet (UV) radiation. Additionally, also as discussed earlier, supplementation with vitamins E and C has demonstrated protective effects against sunburn in a clinical trial by Eberlein-Konig et al. (1998).

Vitamin E supplementation has also demonstrated beneficial effects on DNA repair. In a clinical trial by Mastaloudis et al. (2004), the researchers set out to determine whether 6 weeks of supplementation with vitamins E and C could alleviate exercise-induced DNA damage in ultramarathon runners. The comet assay was used to assess DNA damage in circulating leukocytes at selected time points post-race. Results showed that overall the percentage DNA damage increased at mid-race, but returned to baseline by 2 hours after the race, indicating that the exercise bout induced non-persistent DNA damage. Although DNA damage wasn't affected by supplementation in men, it was shown that one day post-race, women in the treatment group had 62% less DNA damage than women taking placebo (Mastaloudis et al. 2004).

Niacin

In one aspect the composition of the invention includes a daily dose of niacin (vitamin B3).

In one aspect, the niacin is between 7% and 8% of the vitamin/mineral composition of the composition of this invention. In another aspect, niacin is 7.13% of the total active ingredients of the vitamin/mineral composition of the composition of the present invention.

In one aspect of the composition of the present invention, the composition of the present invention comprises a daily dose of about 6 mg to about 35 mg of niacin. In another aspect, the composition of the present invention comprises a daily dose of 20 mg of niacin.

Niacin helps promote internal health. The NHPD has approved the use of niacin for the maintenance of good health (NHPD monograph: niacin).

Vitamin B6

In one aspect the composition of the invention includes a daily dose of vitamin B6.

In one aspect, the vitamin B6 is between 0.8% and 0.9% of the vitamin/mineral composition of the composition of this invention. In a preferred aspect, vitamin B6 is 0.87% of the vitamin/mineral composition of the composition of the present invention.

In one aspect of the composition of the present invention, the composition of the present invention comprises a daily dose of about 0.1 mg to about 100 mg of vitamin B6. In a preferred aspect, the composition of the present invention comprises a daily dose of 1 mg of vitamin B6.

Vitamin B6 promotes internal health. The NHPD has approved the use of vitamin B6 for the maintenance of good health (NHPD monograph: vitamin B6).

Folic Acid

In one aspect the composition of the invention includes a daily dose of folic acid.

In one aspect, the folic acid is between 0.25% and 0.35% of the vitamin/mineral composition of the composition of this invention. In another aspect, folic acid is 0.29% of the vitamin/mineral composition of the composition of the present invention.

In one aspect of the composition of the present invention, the composition of the present invention comprises a daily dose of about 30 mcg to about 1000 mcg of folic acid. In a preferred aspect, the composition of the present invention comprises a daily dose of about 400 mcg of folic acid.

Folic acid helps promote internal health. The NHPD has approved the use of folic acid for the maintenance of good health (NHPD monograph: folic acid).

Vitamin B12

In one aspect the composition of the invention includes a daily dose of vitamin B12.

In one aspect, the vitamin B12 is between 0.0015% and 0.0025% of the vitamin/mineral composition of the composition of this invention. In another aspect, vitamin B12 is 0.0020% of the vitamin/mineral composition of the composition of the present invention.

In one aspect of the composition of the present invention, the composition of the present invention comprises a daily dose of about 2 mcg to about 1000 mcg of vitamin B12. In another aspect, the composition of the present invention comprises a daily dose of about 6 mcg of vitamin B12.

Vitamin B12 promotes internal health. The NHPD has approved the use of vitamin B12 for the maintenance of good health (NHPD monograph: vitamin B12).

Zinc

In one aspect the composition of the invention includes a daily dose of zinc.

In one aspect, the zinc is between 48% and 49% of the vitamin/mineral composition of the composition of this invention. In a preferred aspect, zinc is 48.13% of the vitamin/mineral composition of the composition of the present invention.

In one aspect of the composition of the present invention, the composition of the present invention comprises a daily dose of about 0.1 mg to about 100 mg of zinc. In another aspect, the composition of the present invention comprises a daily dose of about 30 mg of zinc.

Zinc helps promote internal health, helps improve the health and appearance of skin, and also promotes DNA repair. The NHPD has approved the use of zinc for the maintenance of good health (NHPD monograph: zinc). Zinc also contains antioxidant activity and can therefore help maintain skin integrity and appearance by helping combat oxidative stress.

As previously mentioned, antioxidants play a critical role in keeping skin healthy. In a recent review, Chien et al. (2006) reported that zinc promotes antioxidant and immune functions, stabilizes and maintains the structural integrity of biological membranes, and plays a pivotal role in skin and connective tissue metabolism and repair. As well, it was discussed that zinc is an integral constituent of a large number of enzymes including antioxidant enzymes (Chien et al. 2006).

Oral supplementation with antioxidant combinations including zinc has been shown to exhibit beneficial effects on skin appearance and photoageing. For example, Segger & Schönlau (2004) conducted a double-blind, placebo-controlled trial in which women aged 45-73 years participated in testing the efficacy of a proprietary oral supplement on improvement of skin elasticity and roughness. The active ingredients in the treatment included vitamins C and E, carotenoids, selenium, zinc, amino acids and glycosaminoglycans, blueberry extract and Pycnogenol. Results showed that skin elasticity, measured using an optical cutometer, were found to be significantly increased by 9% after 6 weeks of treatment compared with placebo. Skin roughness, as evaluated by three-dimensional microtopography imaging, was found to be significantly lowered by 6% compared with the control group after 12 weeks treatment. The authors concluded that the treatment can potentially improve visible signs of cutaneous ageing (Segger & Schönlau, 2004).

More recently, Skovgaard et al. (2006) investigated the effects of a supplement containing soy, chamomile, white tea, grape seed and tomato extracts, fish protein polysaccharides, vitamins C and E, and zinc on skin appearance. The study was a 6 month, double-blind, placebo controlled, randomized study conducted on healthy post-menopausal females. Clinical grading results showed that the active group had a significantly greater improvement compared to placebo for various face parameters measured after 6 months of treatment, including forehead, periocular and perioral wrinkles, mottled pigmentation, laxity, sagging, under eye dark circles and overall appearance; improvements were also seen for skin on the décolletage after 2, 3 and 6 months of treatment and skin on the hand after 3 and 6 months treatment. Additionally, photo evaluation showed that the active group had a significantly greater improvement on the face after 3 and 6 months for several parameters. Ultrasound measurements showed that the active group had a significantly greater improvement for density measurements after 6 months treatment (Skovgaard et al. 2006). Therefore, supplementation with zinc in combination with other minerals, vitamins and plant extracts with antioxidant properties can not only contribute to the maintenance of health, but also to the outward appearance of skin.

Furthermore, it has been clinically shown that supplementation with zinc can have a positive effect on the antioxidant status of the body and enhance DNA repair. In a study by Prasad et al. (2004), healthy volunteers were administered daily oral zinc supplements or placebo for 8 weeks. Findings indicated that in subjects receiving zinc, plasma levels of lipid peroxidation products and DNA adducts were decreased, whereas no change was observed in the placebo group (Prasad et al. 2004). Roussel et al. (2003) investigated the effects of zinc supplementation for six months on oxidative stress in persons with type 2 diabetes mellitus. Measurement of baseline characteristics indicated that oxidative stress, monitored by plasma TBARS, was increased in individuals with diabetes compared with healthy subjects and an inverse correlation was found between Zn plasma levels and plasma TBARS. After three and six months of zinc supplementation, all of the subjects exhibited plasma zinc values greater than 10.7 micro mol/L. It was found that there was a decrease of plasma TBARS in the zinc supplemented group after six months (15%) with no significant changes observed in oxidative status in the placebo group. The authors concluded that these results are particularly important in light of the deleterious consequences of oxidative stress in persons with diabetes (Roussel et al. 2003).

Selenium

In one aspect the composition of the invention includes a daily dose of selenium.

In some aspect, the selenium is between 0.5% and 2% of the vitamin/mineral composition of the composition of this invention. In another aspect, selenium is 1.13% of the vitamin/mineral composition of the composition of the present invention.

In one aspect of the composition of the present invention, the composition of the present invention comprises a daily dose of about 3.5 mcg to about 400 mcg of selenium. In another aspect, the composition of the present invention comprises a daily dose of about 70 mcg of selenium.

Selenium helps promote internal health, as well as helps improve the health and appearance of skin. The NHPD has approved the use of selenium as an antioxidant for the maintenance of good health (NHPD monograph: selenium). Furthermore, its antioxidant activity can also have a beneficial effect on outward appearance or external beauty. As previously mentioned, antioxidants are intimately involved in the prevention of cellular damage—the common pathway for ageing and numerous diseases. A number of clinical trials have been conducted demonstrating the efficacy of antioxidant supplementation including selenium on the improvement of skin appearance.

For example, Heinrich et al. (2006) investigated the influence of two different antioxidant supplements composed of carotenoids, vitamin E and selenium on parameters related to skin health and skin ageing. In their study, volunteers with healthy, normal skin (type 2) were divided into 3 groups and supplemented for a period of 12 weeks with two different combinations of antioxidants, both including selenium, or placebo. Skin density and thickness were determined by ultrasound measurements following supplementation. The results indicated a significant increase for both parameters in the verum groups. Additionally, roughness, scaling, smoothness and wrinkling of the skin were determined by Surface Evaluation of Living Skin (Visioscan), and it was shown that roughness and scaling were improved by the supplementation with antioxidant micronutrients. No changes were found for any of the parameters in the placebo group (Heinrich et al. 2006). In another study, Greul et al. (2002) found that a combination of antioxidants including carotenoids (beta-carotene and lycopene), vitamins C and E, selenium and proanthocyanidins, led to a selective protection of the skin against irradiation in healthy young female volunteers. The authors concluded that this might be important for future recommendations for immediate suppression of the early phase of UV-induced erythema, including pharmacological prevention of sunburn reactions as well as subsequent chronic skin damage (Greul et al. 2002).

The present invention will be understood by reference to the following non-limiting examples:

Example 1

In one aspect the process of manufacturing the composition of the invention comprises the steps of:
1) Vitamin/mineral pre-blend: blending the vitamins and minerals together in percentage amounts as per table 2 for from about 2 minutes.
2) NU-100™ blend: Mix the seven ingredients of NU-100™ for 1 minute in the percentage amounts as per table 1.

3) AGEOFF™: Blending the NU-100™ blend with the vitamin/mineral pre-blend in percentage breakdown provided in Table 1 for from about 4) Encapsulation: Encapsulation is per normal directions and procedures known in the art. In a preferred aspect the capsule is a size 0 and is filled with the AGEOFF™ powder blend to a capacity target of about 550 mg per capsule plus or minus 5%.

Example 2

In one aspect, the process of manufacturing the composition of the invention comprises the steps of:
1) AGEOFF™ Blending: blending the seven ingredients of NU-100™, the vitamins and minerals together in percentage amounts as per table 2 for from about 2 minutes.
2) Encapsulation: Encapsulation is per normal directions and procedures known in the art. In a preferred aspect the capsule is a size 0 and is filled with the AGEOFF™ powder blend to a capacity target of about 550 mg per capsule plus or minus 5%.

It will be appreciated by those skilled in the art that other variations of the preferred aspect may also be practised without departing from the scope of the invention.

REFERENCES

Albicini, M, Kick J, Hauser B, Ehrmann U, Leverve X, Radermacher P, Speit G, Muth C M. The Orally Effective Mixture of Sod and Gliadin (Glisodin) Protects Against Oxidative DNA Damage. Presented at the 11th Congress of the European Shock Society Jan. 27-30, 2005.

Arciero P J, Bougopoulos C L, Nindl B C, Benowitz N L. Influence of age on the thermic response to caffeine in women. Metabolism. 2000; 49(1):101-107.

Arciero P J, Gardner A W, Calles-Escandon J, Benowitz N L, Poehlman E T. Effects of caffeine ingestion on NE kinetics, fat oxidation, and energy expenditure in younger and older men. Am J Physiol. 1995; 268 (Endorcinol Metab 31): E1192-E1198.

Astrup A, Toubro S, Cannon S, Hein P, Breum L, Madsen J. Caffeine: a double-blind, placebo-controlled study of its thermogenic, metabolic, and cardiovascular effects in healthy volunteers. Am J Clin Nutr. 1990 May; 51(5):759-67.

Baker V A, Hepburn P A, Kennedy S J, Jones P A, Lea L J, Sumpter J P, Ashby J. Safety evaluation of phytosterol esters. Part 1. Assessment of oestrogenicity using a combination of in vivo and in vitro assays. Food Chem Toxicol. 1999 January; 37(1):13-22.

Berube-Parent S, Pelletier C, Dore J, Tremblay A. Effects of encapsulated green tea and Guarana extracts containing a mixture of epigallocatechin-3-gallate and caffeine on 24 h energy expenditure and fat oxidation in men. Br J Nutr. 2005 September; 94(3):432-6.

Cadenas S, Rojas C, Mendez J, Herrero A, Barja G. Vitamin E decreases urine lipid peroxidation products in young healthy human volunteers under normal conditions. Pharmacol Toxicol. 1996 November; 79(5):247-53.

Chantre P, Lairon D. Recent findings of green tea extract AR25 (Exolise) and its activity for the treatment of obesity. Phytomedicine. 2002 January; 9(1):3-8.

Chen J F. The adenosine A(2A) receptor as an attractive target for Parkinson's disease treatment. Drug News Perspect. 2003 November; 16(9):597-604.

Chien X X, Zafra-Stone S, Bagchi M, Bagchi D. Bioavailability, antioxidant and immune-enhancing properties of zinc methionine. Biofactors. 2006; 27(1-4):231-44.

Choo J J. Green tea reduces body fat accretion caused by high-fat diet in rats through beta-adrenoceptor activation of thermogenesis in brown adipose tissue. J Nutr Biochem. 2003 November; 14(11):671-6.

Dulloo A G, Duret C, Rohrer D, Girardier L, Mensi N, Fathi M, Chantre P, Vandermander J. Efficacy of a green tea extract rich in catechin polyphenols and caffeine in increasing 24-h energy expenditure and fat oxidation in humans. Am J Clin Nutr. 1999 December; 70(6):1040-5.

Dulloo A G, Geissler C A, Horton T, Collins A, Miller D S. Normal caffeine consumption: influence on thermogenesis and daily energy expenditure in lean and post-obese human volunteers. Am J Clin Nutr. 1989; 49:44-50.

Dulloo A G, Seydoux J, Girardier L, Chantre P, Vandermander J. Green tea and thermogenesis: interactions between catechin-polyphenols, caffeine and sympathetic activity. Int J Obes Relat Metab Disord. 2000 February; 24(2):252-8.

Eberlein-König B, Placzek M, Przybilla B. Protective effect against sunburn of combined systemic ascorbic acid (vitamin C) and d-alpha-tocopherol (vitamin E). J Am Acad Dermatol. 1998 January; 38(1):45-8.

Erba D, Riso P, Bordoni A, Foti P, Biagi P L, Testolin G. Effectiveness of moderate green tea consumption on antioxidative status and plasma lipid profile in humans. J Nutr Biochem. 2005 March; 16(3):144-9.

Flora S J. Role of free radicals and antioxidants in health and disease. Cell Mol Biol (Noisy-le-grand). 2007 Apr. 15; 53(1):1-2.

Godard M P, Johnson B A, Richmond S R. Body composition and hormonal adaptations associated with forskolin consumption in overweight and obese men. Obes Res. 2005 August; 13(8):1335-43.

Greul A K, Grundmann J U, Heinrich F, Pfitzner I, Bernhardt J, Ambach A, Biesalski H K, Gollnick H. Photoprotection of UV-irradiated human skin: an antioxidative combination of vitamins E and C, carotenoids, selenium and proanthocyanidins. Skin Pharmacol Appl Skin Physiol. 2002 September-October; 15(5):307-15.

Harris R C, Tallon M J, Dunnett M, Boobis L, Coakley J, Kim H J, Fallowfield J L, Hill C A, Sale C, Wise J A. The absorption of orally supplied beta-alanine and its effect on muscle carnosine synthesis in human vastus lateralis. Amino Acids. 2006 May; 30(3):279-89.

Heinrich U, Tronnier H, Stahl W, Béjot M, Maurette J M. Antioxidant supplements improve parameters related to skin structure in humans. Skin Pharmacol Physiol. 2006; 19(4):224-31.

Henning S M, Fajardo-Lira C, Lee H W, Youssefian A A, Go V L, Heber D. Catechin content of 18 teas and a green tea extract supplement correlates with the antioxidant capacity. Nutr Cancer. 2003; 45(2):226-35.

Hill C A, Harris R C, Kim H J, Harris B D, Sale C, Boobis L H, Kim C K, Wise J A. Influence of beta-alanine supplementation on skeletal muscle carnosine concentrations and high intensity cycling capacity. Amino Acids. 2007 February; 32(2):225-33.

Hu G, Bidel S, Jousilahti P, Antikainen R, Tuomilehto J. Coffee and tea consumption and the risk of Parkinson's disease. Mov Disord. 2007 Aug. 21; [Epub ahead of print]

Hussein G, Sankawa U, Goto H, Matsumoto K, Watanabe H. Astaxanthin, a carotenoid with potential in human health and nutrition. J Nat Prod. 2006 March; 69(3):443-9.

Joghataie M T, Roghani M, Negahdar F, Hashemi L. Protective effect of caffeine against neurodegeneration in a model of Parkinson's disease in rat: behavioral and histochemical evidence. Parkinsonism Relat Disord. 2004 December; 10(8):465-8.

O'Connor I, O'Brien N. Modulation of UVA light-induced oxidative stress by beta-carotene, lutein and astaxanthin in cultured fibroblasts. J Dermatol Sci. 1998 March; 16(3): 226-30.

Karppi, T, Rissanen H, Nyyssönen K, Kaikkonen J, Olsson A G, Voutilainen S, Salonen J T. Effects of astaxanthin supplementation on lipid peroxidation. Int J Vitam Nutr Res. 2007 January; 77 (1):3-11.

Katiyar S, Elmets C A, Katiyar S K. Green tea and skin cancer: photoimmunology, angiogenesis and DNA repair. J Nutr Biochem. 2007 May; 18(5):287-96.

Kelly S. *Rhodiola rosea*: A Possible Plant Adaptogen. Altern Med Rev 2001; 6(3):293-302.

Kumar A, Kaundal R K, Iyer S, Sharma S S. Effects of resveratrol on nerve functions, oxidative stress and DNA fragmentation in experimental diabetic neuropathy. Life Sci. 2007 Mar. 6; 80(13):1236-44.

Leveque N, Robin S, Makki S, Muret P, Rougier A, Humbert P. Iron and ascorbic acid concentrations in human dermis with regard to age and body sites. Gerontology. 2003 March-April; 49(2):117-22.

Li C R, Zhou Z, Lin R X, Zhu D, Sun Y N, Tian L L, Li L, Gao Y, Wang S Q. beta-sitosterol decreases irradiation-induced thymocyte early damage by regulation of the intracellular redox balance and maintenance of mitochondrial membrane stability. J Cell Biochem. 2007 Oct. 15; 102(3):748-58.

Mammone T, Akesson C, Gan D, Giampapa V, Pero R W. A water soluble extract from *Uncaria tomentosa* (Cat's Claw) is a potent enhancer of DNA repair in primary organ cultures of human skin. Phytother Res. 2006 March; 20(3): 178-83.

Mastaloudis A, Yu T W, O'Donnell R P, Frei B, Dashwood R H, Traber M G. Endurance exercise results in DNA damage as detected by the comet assay. Free Radic Biol Med. 2004 Apr. 15; 36(8):966-75.

Mireles-Rocha H, Galindo I, Huerta M, Trujillo-Hernandez B, Elizalde A, Cortés-Franco R. UVB photoprotection with antioxidants: effects of oral therapy with d-alpha-tocopherol and ascorbic acid on the minimal erythema dose. Acta Derm Venereol. 2002; 82(1):21-4.

Nachbar F, Korting H C. The role of vitamin E in normal and damaged skin. J Mol Med. 1995 January; 73(1):7-17.

Nagao T, Komine Y, Soga S, Meguro S, Hase T, Tanaka Y, Tokimitsu I. Ingestion of a tea rich in catechins leads to a reduction in body fat and malondialdehyde-modified LDL in men. Am J Clin Nutr 2005; 81:122-9.

Nashita Y., et al. Pre-publication Presentation at Meeting on Carotenoid Research (2007).

NcNulty H., et al. Biochimica et Biophysica (2007), 1768, pp. 167-174.

NHPD monograph: folic acid. [internet] [cited on Sep. 30, 2007] Available from: http://www.hc-sc.gc.ca/dhp-mps/prodnatur/applications/licen-prod/monograph/mono_folate_e.html NHPD monograph: niacin. [internet] [cited on Sep. 30, 2007] Available from: http://www.hc-sc.gc.ca/dhp-mps/prodnatur/applications/licen-prod/monograph/mono_niacin_e.html NHPD monograph: selenium. [internet] [cited on Sep. 30, 2007] Available from: http://www.hc-sc.gc.ca/dhp-mps/prodnatur/applications/licen-prod/monograph/mono_selenium_e.html NHPD monograph: tea. [internet] [cited on Jun. 4, 2007] Available from: http://www.hc-sc.gc.ca/dhp-mps/prodnatur/applications/licen-prod/monograph/mono_tea-the_e.html NHPD monograph: vitamin B12. [internet] [cited on Sep. 30, 2007] Available from: http://www.hc-sc.gc.ca/dhp-mps/prodnatur/applications/licen-prod/monograph/mono_vitamin_b12_e.html NHPD monograph: vitamin B6. [internet] [cited on Sep. 30, 2007] Available from: http://www.hc-sc.gc.ca/dhp-mps/prodnatur/applications/licen-prod/monograph/mono_vitamin_b6_e.html NHPD monograph: vitamin C. [internet] [cited on Sep. 30, 2007] Available from: http://www.hc-sc.gc.ca/dhp-mps/prodnatur/applications/licen-prod/monograph/mono_vitamin_c_e.html NHPD monograph: vitamin D. [internet] [cited on Sep. 30, 2007] Available from: http://www.hc-sc.gc.ca/dhp-mps/prodnatur/applications/licen-prod/monograph/mono_vitamin_d_e.html NHPD monograph: zinc. [internet] [cited on Sep. 30, 2007] Available from: http://www.hc-sc.gc.ca/dhp-mps/prodnatur/applications/licen-prod/monograph/mono_zinc_e.html Niwa, J.; Yamada, S.; Ishigaki, S.; Sone, J.; Takahashi, M.; Katsuno, M.; Tanaka, F.; Doyu, M.; Sobue, G. Disulfide bond mediates aggregation, toxicity, and ubiquitylation of familial amyotrophic lateral sclerosis-linked mutant SOD1. J. Biol. Chem. 2007; 282: 28087-28095.

O'Byrne D J, Devaraj S, Grundy S M, Jialal I. Comparison of the antioxidant effects of Concord grape juice flavonoids alpha-tocopherol on markers of oxidative stress in healthy adults. Am J Clin Nutr. 2002 December; 76(6):1367-74.

O'Connor I, O'Brien N. Modulation of UVA light-induced oxidative stress by beta-carotene, lutein and astaxanthin in cultured fibroblasts. J Dermatol Sci. 1998 March; 16(3): 226-30.

Olas B, Wachowicz B, Majsterek I, Blasiak J. Resveratrol may reduce oxidative stress induced by platinum compounds in human plasma, blood platelets and lymphocytes. Anticancer Drugs. 2005 July; 16(6):659-65.

Pero R W, Amiri A, Sheng Y, Welther M, Rich M. Formulation and in vitro/in vivo evaluation of combining DNA repair and immune enhancing nutritional supplements. Phytomedicine. 2005 April; 12(4):255-63.

Pilarski R, Zieliński H, Ciesiolka D, Gulewicz K. Antioxidant activity of ethanolic and aqueous extracts of *Uncaria tomentosa* (Willd.) D C. J Ethnopharmacol. 2006 Mar. 8; 104(1-2):18-23.

Prasad A S, Bao B, Beck F W, Kucuk O, Sarkar F H. Antioxidant effect of zinc in humans. Free Radic Biol Med. 2004 Oct. 15; 37(8):1182-90.

Roussel A M, Kerkeni A, Zouari N, Mahjoub S, Matheau J M, Anderson R A. Antioxidant effects of zinc supplementation in Tunisians with type 2 diabetes mellitus. J Am Coll Nutr. 2003 August; 22(4):316-21.

Seeram N P, Henning S M, Niu Y, Lee R, Scheuller H S, Heber D. Catechin and caffeine content of green tea dietary supplements and correlation with antioxidant capacity. J Agric Food Chem. 2006 Mar. 8; 54(5):1599-603.

Segger D, Schönlau F. Supplementation with Evelle improves skin smoothness and elasticity in a double-blind, placebo-controlled study with 62 women. J Dermatolog Treat. 2004 July; 15(4):222-6.

Sheng Y, Bryngelsson C, Pero R W. Enhanced DNA repair, immune function and reduced toxicity of C-MED-100, a novel aqueous extract from *Uncaria tomentosa*. J Ethnopharmacol. 2000 February; 69(2):115-26.

Sheng Y, Li L, Holmgren K, Pero R W. DNA repair enhancement of aqueous extracts of *Uncaria tomentosa* in a human volunteer study. Phytomedicine. 2001 July; 8(4):275-82.

Skovgaard G R, Jensen A S, Sigler M L. Effect of a novel dietary supplement on skin aging in post-menopausal women. Eur J Clin Nutr. 2006 October; 60(10):1201-6.

Spasov A A, Wikman G K, Mandrikovl V B, Mironoval I A, Neumoin1VV. A double-blind, placebo-controlled pilot study of the stimulating and adaptogenic effect of *Rhodiola rosea* SHR-5 extract on the fatigue of students caused by stress during an examination period with a repeated low-dose regimen. Phytomedicine. 2000; 7(2) 85-89.

Stout J R, Cramer J T, Mielke M, O'Kroy J, Torok D J, Zoeller R F. Effects of twenty-eight days of beta-alanine and creatine monohydrate supplementation on the physical working capacity at neuromuscular fatigue threshold. J Strength Cond Res. 2006 November; 20(4):928-31.

Stout J R, Cramer J T, Zoeller R F, Torok D, Costa P, Hoffman J R, Harris R C, O'kroy J. Effects of beta-alanine supplementation on the onset of neuromuscular fatigue and ventilatory threshold in women. Amino Acids. 2007 April; 32(3):381-6.

Thiele J J, Schroeter C, Hsieh S N, Podda M, Packer L. The antioxidant network of the stratum corneum. Curr Probl Dermatol. 2001; 29:26-42.

Vivancos M, Moreno J J. beta-Sitosterol modulates antioxidant enzyme response in RAW 264.7 macrophages. Free Radic Biol Med. 2005 Jul. 1; 39(1):91-7.

Wenzel E, Somoza V. Metabolism and bioavailability of trans-resveratrol. Mol Nutr Food Res. 2005 May; 49(5): 472-81.

Westerterp-Plantenga M, Diepvens K, Joosen A M, Berube-Parent S, Tremblay A. Metabolic effects of spices, teas, and caffeine. Physiol Behav. 2006 Aug. 30; 89(1):85-91.

Westerterp-Plantenga M S, Lejeune M P, Kovacs E M. Body weight loss and weight maintenance in relation to habitual caffeine intake and green tea supplementation. Obes Res. 2005 July; 13(7):1195-204.

Wolfram S, Wang Y, Thielecke F. Anti-obesity effects of green tea: from bedside to bench. Mol Nutr Food Res. 2006 February; 50(2):176-87.

Yamashita E. The effects of dietary supplement containing astaxanthin on skin condition. Carotenoid Science. 2006; 10: 91-95.

Yoshida Y, Niki E. Antioxidant effects of phytosterol and its components. J Nutr Sci Vitaminol (Tokyo). 2003 August; 49(4):277-80.

What is claimed is:

1. A composition comprising:
   (a) about 31.25 mg to about 125 mg of forskolin extract standardized to 40% forskolin,
   (b) about 100 mg to about 1000 mg of Astaxanthin extract standardized to 2% astaxanthin,
   (c) about 25 mg to about 200 mg of *Polygonum cuspidatum* extract standardized to 50% trans-resveratrol,
   (d) about 200 mg to about 1000 mg Green Tea extract standardized to about 98% polyphenols, 80% catechins and 45% epigallocatechin-3-gallate (EGCG), and
   (e) about 140 IU to about 840 IU of a superoxide dismutase.

2. The composition of claim 1, wherein said superoxide dismutase is provided as a cantaloupe melon extract standardized to superoxide dismutase.

3. The composition of claim 2 wherein said composition further comprises: beta-sitosterol, a neuroprotectant, rosavins, beta-alanine and salidrosides.

4. A composition comprising:
   (a) from about 14% to about 15% by weight of *Uncaria tomentosa* extract;
   (b) from about 8% to about 9% by weight of *Glycine max* extract;
   (c) from about 5% to about 6% by weight of *Polygonum cuspidatum* extract;
   (d) about 5.87% by weight of beta-alanine;
   (e) from about 7% to about 8% by weight of *Indian colchicum* extract;
   (f) from about 4% to about 5% by weight of a neuroprotectant;
   (g) from about 35% to about 36% by weight of green tea extract;
   (h) from about 11% to about 12% by weight of *Haematococcus pluvialis* extract; and
   (i) from about 5% to about 6% by weight of *Rhodiola rosea* extract.

5. The composition of claim 4 comprising:
   (a) about 14.69% by weight of the *Uncaria tomentosa* extract;
   (b) about 8.81% by weight of the *Glycine max* extract;
   (c) about 5.87% by weight of the *Polygonum cuspidatum* extract;
   (d) about 5.87% by weight of beta-alanine;
   (e) about 7.34% by weight of the *Indian colchicum* extract;
   (f) about 4.41% by weight of the neuroprotectant;
   (g) about 35.39% by weight of the green tea extract;
   (h) about 11.75% by weight of the *Haematococcus pluvialis* extract; and
   (i) about 5.87% by weight of the *Rhodiola rosea*.

6. The composition of claim 5 further comprising a vitamin and/or mineral preparation including: vitamin C as calcium ascorbate; vitamin E as tocopheryl acetate; niacin; vitamin D as cholecalciferol; selenium as L-selenomethionine; vitamin B6 as pyridoxine hydrochloride; folic acid; vitamin B12 as cyanocobalamin; and zinc as zinc chelate.

7. The composition of claim 4 wherein the neuroprotectant is selected from the group consisting of: caffeine and Cha de Bugre.

8. The composition of claim 4 wherein the neuroprotectant is caffeine.

9. The composition of claim 1 further comprising at least one of a pharmaceutically acceptable carrier, an excipient, an emulsifier, a stabilizer, a sweetener, a flavouring agent, a diluent, a coloring agent, a solubilizing agent or combinations thereof.

10. The composition of claim 1, wherein the composition comprises an oral daily unit dosage form.

11. The composition of claim 10, wherein the oral daily unit dosage form is selected from the group consisting of: a capsule, a tablet, a caplet, a sustained release tablet, an enterically coated tablet, a liquid, a gel, a powder, and any combinations thereof.

12. The composition of claim 10, wherein the oral daily unit dosage comprises two or more daily units dosages.

13. The composition of claim 10, wherein said oral daily unit dosage comprises two doses of two capsules per dose.

14. A composition comprising an oral daily unit dosage form of:
(a) about 100 mg to about 400 mg of *Uncaria tomentosa* extract;
(b) about 100 mg to about 400 mg of *glycine max* extract;
(c) about 25 mg to about 200 mg of *Polygunum cuspidatum* extract;
(d) about 50 mg to about 500 mg of beta-alanine;
(e) about 25 mg to about 200 mg of *Indian colchicum* extract;
(f) about 0 mg to about 150 mg of caffeine;
(g) about 200 mg to about 1000 mg of green tea extract;
(h) about 100 mg to 1000 mg of *Haematococcus pluvialis* extract; and
about 50 mg to about 500 mg of *Rhodiola rosea* extract.

15. The composition of claim 14 further comprising:
(a) about 6 mg to about 2000 mg of vitamin C;
(b) about 32 IU to about 1000 IU of vitamin D;
(c) about 10 IU to about 400 IU of vitamin E;
(d) about 6 mg to about 35 mg of niacin;
(e) about 0.1 mg to about 100 mg of vitamin B6;
(f) about 10 mcg about 1000 mcg of folic acid;
(g) about 2 mcg to about 1000 mcg of vitamin B12;
(h) about 1 mg to about 40 mg of zinc; and
(i) about 3.5 mcg to about 400 mcg of selenium.

16. A composition comprising an oral daily unit dosage form of:
(a) about 250 mg of *Uncaria tomentosa* extract;
(b) about 150 mg of *glycine max* extract;
(c) about 100 mg of *Polygonum cuspidatum* extract;
(d) about 100 mg of beta-alanine;
(e) about 125 mg of *Indian colchicum;*
(f) about 250 mg of caffeine;
(g) about 602.4 mg of green tea extract;
(h) about 4 mg of *Haematococcus pluvialis* extract; and
(i) 100 mg of *Rhodiola rosea* extract.

17. The composition of claim 16 further comprising:
(a) about 60 mg of vitamin C;
(b) about 800 IU vitamin D;
(c) about 30 IU vitamin E;
(d) about 20 mg niacin;
(e) about 1 mg vitamin B6;
(f) 400 mcg folic acid;
(g) about 1 mcg vitamin B12;
(h) 30 mg zinc; and
(i) about 70 mcg selenium.

18. The composition in any of claim 1, 2, 3, 4, 5 or 6-17 is for promoting DNA repair, reducing body fat levels, increasing lean body mass, promoting skin health, or reducing the appearance of wrinkles.

19. A composition as claimed in claim 1 for promoting DNA repair further comprising: an extract containing beta-sitosterol.

20. A composition as claimed in claim 1 for decreasing body fat levels and increasing lean body mass further comprising: an extract containing a neuroprotectant and beta-alanine.

21. A composition as claimed in claim 1 for promoting skin health or reducing the appearance of wrinkles further comprising: an extract containing rosavins and salidrosides.

22. The composition of claim 2, wherein said superoxide dismutase is provided in an oral daily unit dosage form of about 100 mg to about 900 mg.

23. A composition comprising:
(a) carboxy alkyl ester provided as an *Uncaria tomentosa* extract standardized to about 8% of carboxy alkyl esters;
(b) beta-sitosterol provided as a *Glycine max* extract standardized to about 40% beta-sitosterol;
(c) resveratrol provided as a *Polygonum cuspidatum* extract standardized to about 50% resveratrol;
(d) forskolin provided as an *Indian colchicum* extract standardized to about 40% forskolin;
(e) epigallocatechin-gallate (EGCG) provided as a green tea extract standardized to 98% polyphenols, 80% catechins and 45% EGCG;
(f) astaxanthin provided as a *Haematococcus pluvialis* extract standarized to 2% astaxanthin; and
(g) rosavin and salidroside provided as a *Rhodiola rosea* extract standardized to 3% rosavins and 1% salidrosides.

24. The composition of claim 23 comprising:
(a) from about 14% to about 15% by weight of the *Uncaria tomentosa* extract;
(b) from about 8% to about 9% by weight of the *Glycine max* extract;
(c) from about 5% to about 6% by weight of the *Polygonum cuspidatum* extract;
(d) from about 5% to about 6% by weight of beta-alanine;
(e) from about 7% to about 8% by weight of the *Indian colchicum* extract;
(f) from about 4% to about 5% by weight of a neurprotectant;
(g) from about 35% to about 36% by weight of the green tea extract;
(h) from about 11% to about 12% by weight of the *Haematococcus pluvialis* extract; and
(i) from about 5% to about 6% by weight of the *Rhodiola rosea* extract.

25. The composition of claim 23 comprising:
(a) about 14.69% by weight of the *Uncaria tomentosa* extract;
(b) about 8.81% by weight of the *glycine max* extract;
(c) about 5.87% by weight of the *Polygonum cuspidatum* extract;
(d) about 5.87% by weight of beta-alanine;
(e) about 7.34% by weight of the *Indian colchicum* extract;
(f) about 4.41% by weight of the neuroprotectant;
(g) about 35.39% by weight of the green tea extract;
(h) about 11.75% by weight of the *Haematococcus pluvialis* extract; and
(i) about 5.87% by weight of the *Rhodiola rosea.*

26. The composition of claim 23 further comprising a neuroprotectant selected from the group consisting of: caffeine and Cha de Bugre.

27. The composition of claim 26 wherein the neuroprotectant is caffeine.

28. A composition comprising:
(a) about 31.25 mg to about 125 mg of forskolin extract standardized to 40% forskolin,
(b) about 100 mg to about 1000 mg of Astaxanthin extract standardized to 2% astaxanthin,
(c) about 25 mg to about 200 mg of *Polygonum cuspidatum* extract standardized to 50% trans-resveratrol,
(d) about 200 mg to about 1000 mg Green Tea extract standardized to about 98% polyphenols, 80% catechins and 45% epigallocatechin-3-gallate (EGCG), and
(e) about 100 mg to about 400 mg of *Uncaria tomentosa* extract standardized to about 8% carboxy alkyl ester.

* * * * *